United States Patent [19]
Ohama

[11] Patent Number: 5,703,152
[45] Date of Patent: Dec. 30, 1997

[54] DEODORIZING COMPOSITION AND DEODORIZING RESIN COMPOSITION CONTAINING IRON (II) COMPOUND

[75] Inventor: Chiaki Ohama, Yokohama, Japan

[73] Assignee: Minato Company, Ltd., Japan

[21] Appl. No.: 501,037

[22] PCT Filed: Dec. 27, 1994

[86] PCT No.: PCT/JP94/02275

§ 371 Date: Aug. 9, 1995

§ 102(e) Date: Aug. 9, 1995

[87] PCT Pub. No.: WO96/20018

PCT Pub. Date: Jul. 4, 1996

[51] Int. Cl.$^6$ .................. C08J 5/10; C08K 3/10; C08L 23/04
[52] U.S. Cl. .................. 524/435; 523/102; 524/423; 524/425
[58] Field of Search .................. 523/102; 524/423, 524/450, 445, 425, 430, 436, 446, 435; 514/502

[56] References Cited

U.S. PATENT DOCUMENTS

| | | |
|---|---|---|
| 4,735,972 | 4/1988 | Shigematso et al. .................. 523/102 |
| 5,015,668 | 5/1991 | Ueda et al. .................. 523/102 |
| 5,534,165 | 7/1996 | Pilosof et al. .................. 252/8.91 |

FOREIGN PATENT DOCUMENTS

| | | |
|---|---|---|
| 60-145143 | 7/1985 | Japan . |
| 61-106161 | 5/1986 | Japan . |
| 62-195062 | 8/1987 | Japan . |
| 63-265975 | 11/1988 | Japan . |
| 2-211240 | 8/1990 | Japan . |
| 4-126153 | 4/1992 | Japan . |

*Primary Examiner*—Vasu Jagannathan
*Assistant Examiner*—U. K. Rajguru
*Attorney, Agent, or Firm*—Lorusso & Loud

[57] ABSTRACT

An aqueous composition or a resin composition is disclosed which can capture bad odor substances such as ammonia, hydrogen sulfide, mercaptan and acetic acid.

These compositions are characterized by containing an iron (II) compound, a chelating agent and a porous substance. The resin compositions include a paint composition, an ink composition and a resin composition for molding.

29 Claims, No Drawings

DEODORIZING COMPOSITION AND DEODORIZING RESIN COMPOSITION CONTAINING IRON (II) COMPOUND

TECHNICAL FIELD

This invention relates to a deodorizing composition and a deodorzing resin composition each containing an iron (II) compound.

BACKGROUND ART

Hitherto, paints have been generally applied to ceilings, interior walls, floors or the like surfaces of buildings or houses for the purpose of beauty and protection thereof. No paints have been known which have a function of deodorization. If a deodorizing property is imparted to a paint to be applied to interior walls, ceilings and floors, then it is possible to deodorize and clean the rooms. This is apparently desirable from the stand point of living environment maintenance.

A liquid deodorizing composition containing an iron (II) compound and a chelating agent dissolved in water is known (JP-A-60-145143 and JP-A-211240). In use, the deodorzing composition is sprayed over a source of bad odors. Alternatively, a liquid absorbing paper-like body, such as wall paper, or a porous material, such as activated carbon or zeolite, is impregnated with the deodorizing composition. There have been no proposals to use such a composition as a paint.

The known deodorizing composition containing an iron (II) compound and a chelating agent is reactive with bad odor substances such as ammonia, amines, hydrogen sulfide, mercaptans. Thus, when air containing odorous substances is contacted with the composition, the substances are reacted with the deodorizing composition and are removed from the air to give odorless air.

The function of the deodorizing composition to remove bad, odor substances is, however, not effective for the removal of a bad odor substance which does not react with ferrous ion. Further, the known composition has a drawback that coloring and precipitation are caused upon reaction with odorous substances.

It is, therefore, a primary object of the present invention to provide a deodorizing composition which contains an iron (II) compound and a chelating agent and which can effectively capture odorous substances that are inert to ferrous ion.

Another object of the present invention is to provide a deodorizing composition which contains an iron (II) compound and a chelating agent and which is substantially free of coloration upon reaction with bad odor substances.

It is a further object of the present invention to provide a deodorizing resin composition containing an iron (II) compound.

It is yet a further object of the present invention to provide a deodorizing paint composition containing an iron (II) compound.

It is yet a further object of the present invention to provide a deodorizing ink composition containing an iron (II) compound.

It is yet a further object of the present invention to provide a deodorizing resin molding composition containing an iron (II) compound.

It is yet a further object of the present invention to provide a deodorizing resin molded article containing an iron (II) compound.

Further objects of the present invention will be easily understood from the description of the present specification.

DISCLOSURE OF THE INVENTION

The present inventor has made an intensive study with a view toward accomplishing the foregoing objects and has completed the present invention.

In accordance with the present invention, there is provided a deodorizing composition comprising an aqueous slurry including an iron (II) compound, a chelating agent, a porous substance and water, wherein the amount of said chelating agent is at least one equivalent per equivalent of said iron (II) compound and wherein the amount of said porous substance is at least 0.5 part by weight per part by weight of said iron (II) compound.

The present invention also provides a deodorizing resin composition comprising an aqueous slurry including an iron (II) compound, a chelating agent, a porous substance, a resin and water, wherein the amount of said chelating agent is at least one equivalent per equivalent of said iron (II) compound and wherein the amount of said porous substance is at least 0.5 part by weight per part by weight of said iron (II) compound.

The present invention further provides a deodorizing paint composition comprising an aqueous slurry including an iron (II) compound, a chelating agent, a porous substance, a pigment, a resin and water, wherein the amount of said chelating agent is at least one equivalent per equivalent of said iron (II) compound and wherein the amount of said porous substance is at least 0.5 part by weight per part by weight of said iron (II) compound.

The present invention further provides a deodorizing ink composition comprising an aqueous paste including an iron (II) compound, a chelating agent, a porous substance, a coloring agent, a resin and water, wherein the amount of said chelating agent is at least one equivalent per equivalent of said iron (II) compound and wherein the amount of said porous substance is at least 0.5 part by weight per part by weight of said iron (II) compound.

The present invention further provides a deodorizing shaped body of a composition comprising water, an iron (II) compound, a chelating agent, a porous substance, a resin and a water-soluble plasticizer, wherein the amount of said chelating agent is at least one equivalent per equivalent of said iron (II) compound and wherein the amount of said porous substance is at least 0.5 part by weight per part by weight of said iron (II) compound.

The present invention further provides a deodorizing resin composition for molding, comprising a pellet including an iron (II) compound, a chelating agent, a porous substance, a water-soluble plasticizer, a resin and water, wherein the amount of said chelating agent is at least one equivalent per equivalent of said iron (II) compound and wherein the amount of said porous substance is at least 0.5 part by weight per part by weight of said iron (II) compound.

The present invention further provides a deodorizing resin molded article comprising an iron (II) compound, a chelating agent, a porous substance, a water-soluble plasticizer, a resin and water, wherein the amount of said chelating agent is at least one equivalent per equivalent of said iron (II) compound and wherein the amount of said porous substance is at least 0.5 part by weight per part by weight of said iron (II) compound.

BEST MODE FOR PACTICING THE INVENTION

The deodorizing composition according to the present invention includes an aqueous slurry containing water, an iron (II) compound, a chelating agent and a porous substance.

As the iron (II) compounds, there may be mentioned inorganic acid salts of iron (II) such as ferrous sulfate, ferrous chloride, ferrous bromide and ferrous iodide and organic acid salts of iron (II) such as ferrous gallate, ferrous malate and ferrous fumarate.

Any chelating agent may be used as long as it can form a chelate with iron ion. Illustrative of suitable chelating agents are polyaminocarboxylic acids and water-soluble salts thereof such as ethylenediaminetetraacetic acid (EDTA), iminodiacetic acid, diethylenetrimaninepentaacetic acid, nitrilotriacetic acid, diaminopropanetetraacetic acid, hydroxyethyliminodiacetic acid, 1,2-diaminocyclohexanetetraacetic acid, hydroxyethylethylenediaminetriacetic acid, dihydroxyethylglysine; polyaminophosphoric acids and water-soluble salts thereof such as ethylenediaminetetrakis(methylenephosphonic acid) and nitrilotris(methylenephosphonic acid); oxycarboxylic acids and water-soluble salts thereof such as citric acid and gluconic acid; and alkyldiphosphonic acids and water-soluble salts thereof. These chelating agents may be used by themselves or in the form of a mixture. The use of polyaminocarboxylic acids (such as EDTA and iminodiacetic acid) or water-soluble salts (such as sodium salts and potassium salts) thereof is particularly preferred.

The porous substance may be, for example, a crystalline silicate such as silicalite, zeolite, montmorillonite, sepiolite or a mixture thereof; clay such as flake, active flake, diatomaceous earth, kaoline, bentonite, kibushi clay and gairome clay; and metal oxides such as silica, alumina, silica gel, magnesia, titania, zirconia, silica/alumina and silica/titania. The porous substance has an average particle diameter of 0.1–50 µm, preferably 0.5–20 µm, more preferably 0.5–10 µm.

The iron (II) compound is contained in the aqueous slurry in an amount of 1–25 parts by weight, preferably 5–20 parts by weight per 100 parts by weight of the water. The amount of the chelating agent is at least one equivalent, preferably 1.2–5 equivalents, more preferably 1.2–2 equivalents, per equivalent of the iron (II) compound. The amount of the porous substance is at least 0.5 parts by weight, preferably 1–20 parts by weight, more preferably 2–10 parts by weight, per part by weight of the iron (II) compound. The content of the porous substance in the aqueous slurry is 5–80% by weight, preferably 10–60% by weight, based on the total composition. The aqueous slurry has a pH of 6–10, preferably 7–9, more preferably 7.5–8.5.

The aqueous slurry may be prepared as follows. An aqueous solution containing the iron (II) compound and the chelating agent is first prepared. Then the solution is homogeneously mixed with the porous substance. In this case, a dispersing agent (surfactant) or a viscosity increasing agent (water-soluble polymer) may be added, if desired. The resulting mixture is added with a pH controlling agent which may be selected from acidic substances and alkaline substances according to the desired pH of the aqueous slurry. An inorganic or organic acid is used as the acidic substance. The use of an organic acid is preferred. Sodium hydrogencarbonate, potassium hydrogencarbonate, sodium carbonate, sodium hydroxide, etc. may be used as the alkaline substance.

In the aqueous slurry of the present invention, the iron (II) ion is stabilized by reaction with the chelating agent and the iron (II) ion thus stabilized by the chelating agent is further stabilized by being adsorbed by the porous substance. Thus, the aqueous slurry whose pH has been adjusted to 7–10 substantially does not turn blue even when potassium ferricyanide, which is a detecting gent for iron (II) ion, is added thereto.

Notwithstanding the stabilization of the iron (II) ion, the aqueous slurry can exhibit an excellent capturing effect for various bad odor substances. For example, it is possible to deodorize odorous substance-containing air by contact with the aqueous slurry and by capturing the odorous substance with the aqueous slurry. The odorous substance-capturing effect of the aqueous slurry according to the present invention is based on both the chemical action of the iron (II) compound and the physical action of the porous substance. Odorous substances which do not react with iron (II) ion are captured (adsorbed) by the porous substance.

In use, the aqueous slurry of the present invention may be sprayed as such or after dilution with water over a source of bad odors. Spraying the slurry in odorous substance-containing air is also adopted. It is also possible to remove the odorous substance from odorous substance-containing gas by blowing the gas into the aqeuous slurry.

The aqueous slurry according to the present invention may be used as an additive for the production of deodorizing articles. For example, the aqueous slurry is mixed and kneaded with an adsorbent such as activated carbon, zeolite, alumina, silica or magnesia, and the resulting kneaded mass is molded and dried, thereby to give a shaped, deodorizing article. The shaped article may be in any desired form such as a pellet, a plate, a block or a receptacle. The aricle can exhibit suitable deodorizing properties even in a dried state. The aqueous slurry of the present invention can be impregnated in a fibrous material such as a paper, a non-woven fabric, a woven fabric or a fiber and dried to give a fibrous deodorizing article.

The aqueous slurry may also be used as a component for the preparation of a resinous composition such as a paint composition, an ink composition or a molding resin composition. The resin may be a polymer or a prepolymer thereof. Examples of suitable resins include thermoplastic resins, thermosetting resins, photosensitive resins, naturally occurring polymers and synthetic rubbers. Details of resinous compositions will be described below.

(1) Paint Composition:

The paint composition contains water, an iron (II) compound, a chelating agent, a porous substance, a pigment and a resin. If desired, auxiliary components such as a dispersing agent (surfactant), a viscosity increasing agent (water-soluble polymer) and a pH controlling agent may be incorporated into the paint composition.

Resins conventionally used in aqueous paints may be employed. Illustrative of suitable resins are water-soluble resins (inclusive of aqueous alkali-soluble resins) such as alkyd resins, melamine resins, urea resins, phenol resins, acrylic resins, epoxy resins, polybutadiene resins, polyvinyl alcohols, carboxymethyl cellulose and casein; and water-insoluble resins such as vinyl acetate resins, styrene-butadiene resins, acrylate resins, silicone resins, fluoroethylene resins and synthetic rubbers.

As the pigment, there may be used an extender such as talc, kaolin, calcium carbonate, magnesium oxide, magnesium hydroxide, magnesium carbonate, magnesium silicate, aluminum oxide, aluminum hydroxide or anhydrous silicate; a white inorganic pigment such as titanium dioxide, white lead, molybdenum white, zinc oxide or lithopone; a colored inorganic pigment such as mica-like iron oxide, minium, chrome yellow, black iron oxide, ultramarine, iron blue, cobalt oxide, titanium black, titanium yellow, molybdenum red, vermilion, litharge or cobalt blue; or an organic pigment such as an azo pigment.

The paint composition may be prepared by mixing the aqueous slurry with the pigment, then with the auxiliary components such as a dispersing agent, a viscosity increasing agent and a pH controlling agent and finally with the resin. The resin is mixed in the form of an aqueous solution when it is soluble in water or in the form of an aqueous dispersion when it is insoluble in water.

The amount of the resin in the paint composition is generally 5–25% by weight, preferably 10–20% by weight. The total amount of the pigment and the porous substance is generally 10–80% by weight, preferably 15–65% by weight, more preferably 20–60% by weight. The content of the iron (II) compound in the composition is generally 1–15% by weight, preferably 2–10% by weight.

In one preferred embodiment, the paint composition uses the extender and the white pigment in combination. The extender is preferably magnesium oxide, magnesium hydroxide, magnesium carbonate, aluminum oxide, silica, talc, silicate or an aluminum hydroxide, while the white pigment is preferably an inorganic white pigment such as titanium dioxide, zinc oxide or lithopone. Particularly preferred is a combination of titanium dioxide with lithopone. While the proportion of the extender and the white pigment is not specifically limited, the white pigment is generally used in an amount of 50–400 parts by weight, preferably 100–200 parts by weight, per 100 parts by weight of the extender. In the case of the combination of titanium dioxide with lithopone, lithopone is generally used in an amount of 5–30 parts by weight, preferably 15–20 parts by weight, per 100 parts by weight of titanium dioxide. The paint composition generally has a pH of 7–10, preferably 7.5–9.

If desired, a blowing agent may be incorporated into the paint composition. Any blowing agent may be used as long as it is stable at room temperature but is dcapable of generating a gas such as $N_2$, $CO_2$, $NH_3$ or a hydrocarbon when heated. Illustrative of suitable blowing agents are azonitro compounds such as azobisisobutylonitrile; diazoamino compounds such as diazoaminobenzene; azodicarbonamides such as diazenedicarboxyamide, 1,1'-azobisformamide, azodicarboxyamide and 1,1'-azobiscarbamide; hydrazine compounds such as benzenesulfohydrazine; carbonates such as ammonium carbonate and sodium hydrogencarbonate; and microcapsules (for example, Matsumoto Microsphere F-50 manufactured by Matsumoto Yushi Inc.) having shell walls of a polymer such as a vinylidene chloride polymer within which a low boiling point hydrocarbon is encapsulated. Such blowing agents causes expansion upon being heated at a temperature of 100° C. or more, occasionally 130° C. or more. Thus, when a coating of the paint composition is heated at a temperature higher than the expansion starting temperature thereof, the blowing agent causes expansion in the coating to give a porous foamed layer having an increased surface area. Thus, the foamed layer has an improved efficiency of the odorous gas with the deodorizing component, i.e. iron (II) compound, and with the porous substance, so that effective deodorization can be made. The content of the blowing agent in the paint composition is not specifically limited but is generally 1–20% by weight, preferably 1–10% by weight.

The paint composition according to the present invention is incombustible and shows excellent flame proofing properties and, thus, can be suitably used as a deodorizing, flame-proofing paint to be applied on various surfaces such as of wall-papers, leather, animal skin products, papers, fibers, fibrous products, non-woven fabrics, steel, glass, tiles, wood, boards, plastic films and plastic plates. A room having a ceiling, a floor and/or a wall applied with the paint composition can remove unpleasant odors therefrom and can maintain comfortable environment. When a blowing agent is incorporated into the paint composition, a coating of the composition can give a porous layer by heating.

(2) Ink Composition:

The ink composition according to the present invention is a paste-like material containing an iron (II) compound, a chelating agent, a porous substance, a coloring agent, a resin and water. If desired, auxiliary components such as an extender, a dispersing agent, a viscosity increasing agent a pH controlling agent and a blowing agent may be incorporated into the ink composition.

As the resin, there may be mentioned a water-soluble resin, an alkali-soluble resin, a water-insoluble resin, a UV-hardenable resin and an IR-hardenable resin. The resin is present in the ink composition in the form of an aqueous solution when it is soluble in water or in the form of an aqueous dispersion when it is insoluble in water. As the coloring agent, a colored pigment or dye may be used. A colored pigment is generally used. The amount of the resin in the ink composition is generally 5–35% by weight, preferably 10–30% by weight. The content of the iron (II) compound in the composition is generally 1–15% by weight, preferably 2–10% by weight.

The ink composition according to the present invention is useful as a printing ink such as for screen printing, flexographic printing, gravure printing and offset printing. Printed sheets obtained with the ink composition exhibit deodorizing properties.

(3) Resin Composition for Forming Shaped Articles:

The resin composition for forming a shaped article contains an iron (II) compound, a chelating agent, a porous substance, a water-soluble plasticizer and a resin. If desired, auxiliary components such as a pigment, starch, a filler and a blowing agent may be incorporated into the composition. As the resin, there may be used various conventionally known resins such as thermoplastic resins and thermosetting resins. Illustrative of water-soluble plasticizers are polyhydric alcohols such as glycerin, polyglycerin, polyethylene glycol, polypropylene glycol and pentaerythrytol and water-soluble resins. The amount of the resin in the composition is generally 25–80% by weight, preferably 30–60% by weight. The content of the water-soluble plasticizer is generally 5–30% by weight, preferably 10–20% by weight. The content of the iron (II) compound in the composition is generally 1–15% by weight, preferably 2–10% by weight. The filler may be those previously described as the porous substance and extender. The amount of the filler is generally 5–35% by weight, preferably 10–25% by weight.

The molding resin composition according to the present invention may be prepared by kneading the above-described aqueous slurry with the water-soluble plasticizer, resin and auxiliary components together at a temperature higher than the melting point of the resin, the kneaded mixture being molded into pellets.

The molded resin article according to the present invention may be obtained by melting and molding the thus obtained pellets. The molded article may be in any various form such as a sheet, a film, a receptacle and a string.

EXAMPLES

The present invention will be further described in detail below by way of the examples. Parts and percentages are by weight.

Example 1

Into 100 parts of water were dissolved 18 parts of ferrous sulfate heptahydrate ($FeSO_4.7H_2O$) and 15 parts of disodium ethylenediaminetetraacetate (EDTA-2Na, a chelating agent), with which were homogeneously mixed with stirring 50 parts of acid clay and 1 part of a nonionic surfactant (RHEODOL manufactured by Kao Co., Ltd., a dispersing agent). Then, the pH of the resulting mixture was adjusted to about 8 by addition of sodium hydrogencarbonate (a pH controlling agent) to obtain an aqueous slurry [I] having an equivalency ratio of the ferrous sulfate to the chelating agent of about 1:1.4.

No coloring was observed when 10 ml of a 10% aqueous potassium ferricyanate solution was added into 100 ml of the aqueous slurry [I].

For the purpose of comparison, 10 ml of the ferricyanate solution was mixed with 100 ml of an aqueous solution containing 18 parts of ferrous sulfate and 2 parts of EDTA-2Na with stirring. The solution turned blue.

The aqueous slurry [I] was found to satisfactorily capture ammonia, trimethylamine, methylmercaptan, hydrogen sulfide, sulfurous acid gas, acetic acid and butyric acid.

Example 2

An aqueous slurry [II] was prepared in the same manner as described in Example 1 except that 15 parts of sodium nitrilotriacetate were substituted for 15 parts of EDTA-2Na. The equivalency ratio of the ferrous sulfate to the chelating agent of the aqueous slurry [II] is about 1:1.8. The aqueous slurry [II], similar to the aqueous slurry [I] in Example 1, was found to cause no coloring upon addition of potassium ferricyanate and to exhibit good odorous substance-capturing characteristics.

Example 3

Example 1 was repeated in the same manner as described except that 50 parts of acid clay was replaced by other porous substances as shown in Table 1, thereby to obtain aqueous slurries [III]-[VI]. These slurries were found to show properties similar to aqueous slurry [I].

TABLE 1

| Aqueous Slurry | Porous Substance | Amount (part) |
|---|---|---|
| III | zeolite | 50 |
| IV | sepiolite | 10 |
| V | Titanic | 20 |
| VI | silica | 50 |

Example 4

A paint composition A (pH: about 8) having the formulation shown in Table 2 was prepared.

TABLE 2

| Ingredient | Amount (part) |
|---|---|
| Aqueous Slurry [I] | 100 |
| Resin Emulsion A | 30 |
| Magnesium oxide | 5 |
| Lithopone | 20 |
| Dispersing agent | 2 |
| Viscosity increasing agent | 8 |

The components shown in Table 2 are as follows:
(1) Resin Emulsion A
An aqueous emulsion (Trade name: POLYSOL manufactured by Showa Polymer Co., Ltd.) containing an ethylene/vinyl acetate copolymer as a major ingredient, Solid content: about 55%

(2) Dispersing Agent
Nonionic surfactant (RHEODOL manufactured by Kao Co., Ltd.)
(3) Viscosity Increasing Agent
Aqueous nonionic viscosity-increasing agent (ADEKANOL UH-420, manufactured by Asahi Denka Co., Ltd.), Solid content: 30%, Viscosity: 20,000 cPs The thus obtained composition A was tested for its performance as follows:

Measurement of Deodorizing Performance of Composition

[Object]

Deodorizing property of the composition for ammonia, trimethylamine, methylmercaptan, hydrogen sulfide and acetic acid was evaluated.

[Preparation of Sample]

The composition A (20 g) was applied onto a surface of a round filter paper having a diameter of 20 cm. The filter was then dried at 120° C. to obtain a sample A.

[Test Method]

The sample A was placed in a plastic bag (3 liters). Then the bag was filled with an odorous substances-containing air and sealed. The concentration of the odorous substances (ppm by volume) at various time was measured at room temperature.

[Test Results]

The results were as summarized in Table 3.

TABLE 3

| | Concentration (ppm by volume) Time Passage (minutes) | | | |
|---|---|---|---|---|
| Odorous Substance | 0 | 10 | 50 | 100 |
| Ammonia | 470 | 150 | 10 | 0 |
| Trimethylamine | 55 | 30 | 8 | 0 |
| Methylmercaptan | 250 | 170 | 20 | 0 |
| Hydrogen sulfide | 600 | 200 | 0 | 0 |
| Acetic acid | 70 | 38 | 6 | 0 |

Example 5

The composition A obtained in Example 4 (100 parts) was mixed with 15 parts of an aqueous resin emulsion B (Trade name: POLYSOL AT-191 manufactured by Showa Polymer Co., Ltd.) containing an acrylate polymer as a major ingredient and 15 parts of titanium dioxide to obtain a white paint composition B having a pH of about 8.

The paint composition B thus obtained was applied to a heat resistant plate and dried at 120° C. to form a coating.

The coated surface was placed above a flame of a gas burner. The coating showed good flame resistance and did not smoke.

Example 6

The paint composition B obtained in Example 5 was placed in a petri dish and allowed to stand for two weeks. No mold was formed.

Example 7

A 28% aqueous ammonia (1 ml) was applied onto the coated filter paper obtained in Example 4 and onto the coated plate obtained in Example 5. No discoloration of the coated surface was observed.

Example 8

The composition A obtained in Example 4 (100 parts) was mixed with 5 parts of a blowing agent A to obtain a foamable paint composition C. The blowing agent A was microcapsulated compound of a low boiling point hydrocarbon (Trade name: Matsumoto Microsphere F-50 manufactured by Matsumoto Yushi Co., Ltd., particle size: 10–20 μm, foam initiation temperature: 100°–105° C.). The composition C (20 g) was applied to a surface of a round filter paper having a diameter of 20 cm and the coating was heated at 140° C. for 2 minutes to obtain a foamed layer. The thus obtained filter paper was tested for its deodorizing characteristics in the same manner as described in Example 4. The results are summarized in Table 4.

TABLE 4

| Odorous Substance | Concentration (ppm by volume) Time Passage (minutes) | | | |
|---|---|---|---|---|
| | 0 | 10 | 50 | 100 |
| Ammonia | 500 | 120 | 5 | 0 |
| Trimethylamine | 60 | 25 | 5 | 0 |
| Methylmercaptan | 270 | 140 | 10 | 0 |
| Hydrogen sulfide | 500 | 100 | 0 | 0 |
| Acetic acid | 60 | 20 | 0 | 0 |

Example 9

The composition B obtained in Example 5 (100 parts) was mixed with 5 parts of the blowing agent A to obtain a foamable paint composition D.

The paint composition D was applied to a heat resistant plate and dried at 140° C. for 2 minutes to form a foamed coating having a thickness of about 2 mm.

The coated surface was placed above a flame of a gas burner. The coating showed good flame resistance and did not smoke.

Example 10

The composition A obtained in Example 4 (100 parts) was mixed with 20 parts of the aqueous emulsion B obtained in Example 5 and 20 parts of titanium black to obtain a black ink composition.

Example 11

The aqueous slurry [I] (20 parts) was mixed with 10 parts of silica, 10 parts of glycerin and 60 parts of polycaprolactone. The mixture was kneaded at 95° C. and pelettized with an extruder. The pellets were then extruded to form a sheet.

I claim:

1. A deodorizing composition comprising an aqueous slurry including a ferrous compound, a chelating agent and a porous substance, wherein the amount of said chelating agent is at least one equivalent per equivalent of said ferrous compound and wherein the amount of said porous substance is at least 0.5 part by weight per part by weight of said ferrous compound.

2. A composition as claimed in claim 1, wherein said ferrous compound is selected from the group consisting of ferrous sulfate, ferrous chloride, ferrous bromide and ferrous iodide and said porous substance is at least one member selected from the group consisting of zeolite, sepiolite, acid clay, silica and titania.

3. A composition as claimed in claim 1, wherein said slurry has a pH of 7–9.

4. A composition as claimed in claim 1, wherein said aqueous slurry additionally includes a resin.

5. A composition as claimed in claim 4, wherein said resin is present in the form of a solution or emulsion in said water.

6. A composition as claimed in claim 4, wherein said aqueous slurry additionally includes a blowing agent.

7. A composition as claimed in claim 4, wherein said aqueous slurry additionally includes a pigment.

8. A composition as claimed in claim 7, wherein said pigment is a white pigment.

9. A composition as claimed in claim 8, wherein said white pigment is a mixture of titanium oxide (IV) with lithopone.

10. A composition as claimed in claim 7, wherein said aqueous slurry additionally includes an extender.

11. A composition as claimed in claim 10, wherein said extender is magnesium oxide or magnesium hydroxide.

12. A composition as claimed in claim 7, wherein said aqueous slurry additionally includes a blowing agent.

13. A composition as claimed in claim 4, wherein said aqueous slurry additionally includes a coloring agent.

14. A composition as claimed in claim 13, wherein said coloring agent is a color pigment.

15. A composition as claimed in claim 13, wherein said aqueous slurry additionally includes an extender.

16. A composition as claimed in claim 13, wherein said aqueous slurry additionally includes a blowing agent.

17. A deodorizing composition comprising a dried mass of said aqueous slurry according to claim 1.

18. A deodorizing composition in the form of pellets, comprising water, a ferrous compound, a chelating agent, a porous substance, a resin and a water-soluble plasticizer, wherein the amount of said chelating agent is at least one equivalent per equivalent of said ferrous compound and wherein the amount of said porous substance is at least 0.5 part by weight per part by weight of said ferrous compound.

19. A composition as claimed in claim 18, further comprising a filler.

20. A deodorizing shaped body obtained by molding a composition according to claim 18, at a temperature sufficient to melt said resin.

21. A deodorizing shaped body of a composition comprising water, a ferrous compound, a chelating agent, a porous substance, a resin and a water-soluble plasticizer, wherein the amount of said chelating agent is at least one equivalent per equivalent of said ferrous compound and wherein the amount of said porous substance is at least 0.5 part by weight per part by weight of said ferrous compound.

22. A shaped body as claimed in claim 21, further comprising a filler.

23. A shaped article obtained by drying a shaped body according to claim 21.

24. A deodorizing composition in accordance with claim 1 wherein said ferrous compound is selected from the group consisting of ferrous chloride, ferrous bromide and ferrous iodide.

25. A deodorizing composition in accordance with claim 1 wherein said ferrous compound is an organic acid salt of iron (II).

26. A deodorizing composition in accordance with claim 18 wherein said ferrous compound is selected from the group consisting of ferrous chloride, ferrous bromide and ferrous iodide.

27. A deodorizing composition in accordance with claim 18 wherein said ferrous compound is an organic acid salt of iron (II).

28. A deodorizing shaped body in accordance with claim 21 wherein said ferrous compound is selected from the group consisting of ferrous chloride, ferrous bromide and ferrous iodide.

29. A deodorizing shaped body in accordance with claim 21 wherein said ferrous compound is an organic acid salt of iron (II).

* * * * *